(12) United States Patent
Cornell et al.

(10) Patent No.: US 9,675,433 B2
(45) Date of Patent: Jun. 13, 2017

(54) ADAPTER FOR DENTAL MILLING BLANK

(71) Applicant: Jensen Industries Incorporated, North Haven, CT (US)

(72) Inventors: Donald F. Cornell, Madison, CT (US); David J. Stine, Cheshire, CT (US)

(73) Assignee: Jensen Industries Inc., North Haven, CT (US)

( * ) Notice: Subject to any disclaimer, the term of this patent is extended or adjusted under 35 U.S.C. 154(b) by 276 days.

(21) Appl. No.: 14/093,147

(22) Filed: Nov. 29, 2013

(65) Prior Publication Data

US 2014/0147225 A1    May 29, 2014

Related U.S. Application Data

(60) Provisional application No. 61/731,262, filed on Nov. 29, 2012, provisional application No. 61/767,579, filed on Feb. 21, 2013.

(51) Int. Cl.
*A61C 13/00* (2006.01)
*B23Q 3/06* (2006.01)

(52) U.S. Cl.
CPC ........... *A61C 13/0022* (2013.01); *B23Q 3/06* (2013.01); *B23Q 3/062* (2013.01); *A61C 13/0004* (2013.01); *Y10T 409/309016* (2015.01); *Y10T 428/24008* (2015.01); *Y10T 428/24777* (2015.01)

(58) Field of Classification Search
None
See application file for complete search history.

(56) References Cited

U.S. PATENT DOCUMENTS

| | | | | |
|---|---|---|---|---|
| 2003/0132539 A1* | 7/2003 | Althoff | ............. | A61C 13/0022 264/16 |
| 2004/0072121 A1* | 4/2004 | Filser | ................ | A61C 13/0022 433/25 |
| 2009/0130634 A1* | 5/2009 | Ganley | ............. | A61C 13/0022 433/206 |
| 2009/0275000 A1* | 11/2009 | Jung | ................. | A61C 13/0004 433/223 |
| 2011/0253734 A1* | 10/2011 | Guggenmos | ....... | A61C 13/0004 433/167 |
| 2015/0174716 A1* | 6/2015 | Suyama | ................... | B23Q 3/06 409/225 |

\* cited by examiner

*Primary Examiner* — David Sample
*Assistant Examiner* — Nicholas W Jordan
(74) *Attorney, Agent, or Firm* — Pepper Hamilton LLP

(57) ABSTRACT

Adapters and dental mill blanks are provided which permit use of dental mill blanks of various shapes in dental mills designed for use with only a single shape. In particular, a mill blank assembly may include an adapter which allows for the use of rectangular, framed dental blanks in milling machines designed for use with puck-like milling blanks.

3 Claims, 12 Drawing Sheets

ADAPTER FOR DENTAL MILLING BLANK

CROSS REFERENCE TO RELATED APPLICATIONS

This application claims priority to U.S. Provisional Patent Application Nos. 61/731,262 filed Nov. 29, 2012 and 61/767,579 filed Feb. 21, 2013, each of which is incorporated herein by reference in its entirety.

TECHNOLOGY FIELD

This disclosure relates to an adapter for a dental milling blank for use in a dental milling machine. More particularly, this disclosure relates to an adapter for use in dental milling machines for milling round "puck" dental blanks for use with non-"puck" shaped dental blanks. More particularly, this disclosure relates to an adapter for use in a puck milling machine which allows for framed and/or frameless rectangular milling blanks.

BACKGROUND

With modern technology, dental restorations can be prepared in dental milling machines found not only in sophisticated, dedicated dental labs, but also in dental offices. Such milling machines are in common usage in the United States and worldwide. Milling blanks for such machines are also well known. They come in several different varieties, most notably "puck" mill blanks, and framed mill blanks. Milling machines typically contain a single receiver for receiving one of these mill blank types. Thus, the milling machine technicians are limited in their choice of materials, if they do not wish to go through the added expense of an additional mill or the added time required to change receivers, if that is even possible on their milling machine. For this reason, it is desirous to have an adapter for using framed dental blanks in a mill designed for puck mill blanks. It is further desirous to have non-puck frameless mill blanks for use in puck mills.

SUMMARY

Some embodiments provide an adapter for use in a dental milling machine having a dental blank receiver for engaging dental blanks having a first shape, the adapter comprising a receiver end wall adapted to engage the receiver of the dental milling machine; and two side walls adapted for holding a dental mill blank of a second shape. In some such embodiments, the first shape is a puck, and the second shape is a rectangle. In some embodiments, the shaped dental blank comprises a frame. In other embodiments, the shaped dental blank is frameless.

Some embodiments provide an adapter for a dental mill blank having a support lip, the adapter comprising a receiver end wall, two sidewalls opposite each other and extending from the receiver end wall, wherein the two sidewalls and the receiver end wall define peripheral walls of an aperture for receiving the mill blank, wherein the peripheral walls are provided with a support shoulder for engaging the support lip of the mill blank. Some embodiments further provide an end wall connecting each of the two sidewalls opposite the receiver end wall.

In some embodiments, the receiver end wall defines a locating flange for engaging the receiver of the milling machine wherein the locating flange is positioned so as to place the adapter in proper location for precision milling.

In some embodiments, the adapter is configured to support a frame supporting milling material. In other embodiments, the adapter is configured to support frameless milling material. In some embodiments, the adapter is configured to interchangeably support either framed or frameless milling material.

Some embodiments provide a dental mill blank comprising a solid singular piece of milling material defining an outer peripheral edge; the outer peripheral edge further defining a support lip extending outwardly therefrom for engaging a support shoulder in a dental mill adapter. In some embodiments, the mill blank is generally rectangular. In some embodiments, the support lip extends substantially along three sides of the rectangular dental mill blank.

Some embodiments provide a dental mill blank comprising: a solid singular piece of milling material defining a non-circular outer peripheral edge; wherein a portion of the outer peripheral edge defines a receiver end which is arc-shaped such that it can engage a puck receiver in a dental milling machine and the remaining portion defines a non-circular shape. In some embodiments, the dental mill blank is generally rectangular except for the arc-shaped receiver end. In some embodiments, the arc-shaped receiver end further defines a locating flange.

Some embodiments provide a mill blank assembly comprising a mill blank material, and an adapter for use in a milling machine adapted to hold the mill blank material. In some embodiments, the mill blank material comprises a framed mill blank. In some embodiments, the mill blank material comprises a frameless mill blank. In some embodiments, the adapter further comprises a receiver end adapted to be secured in a receiver of a milling machine. In some embodiments, the adapter further comprises a receiver end wall, two sidewalls opposite each other and extending from the receiver end wall, wherein the two sidewalls and the receiver end wall define peripheral walls of an aperture for receiving the mill blank material, wherein the peripheral walls are provided with a support shoulder for engaging the support lip of the mill blank.

Some embodiments provide a dental milling apparatus comprising a dental milling machine having a receiver adapted for receiving and holding shaped dental blanks of a first shape, an adapter for holding shaped dental blanks of a second shape, the adapter further comprising a receiver end wall adapted to engage the receiver of the dental milling machine. In some embodiments, the first shape is a puck, and the second shape is generally rectangular. In some embodiments, the rectangular shaped dental blank comprises a frame.

These and other embodiments are described herein or will be apparent in light of the disclosure herein.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF ILLUSTRATIVE EMBODIMENTS

Some embodiments provide an adapter for use in a dental milling machine having a dental blank receiver for engaging dental blanks having a first shape, the adapter comprising a receiver end wall adapted to engage the receiver of the dental milling machine; and two side walls adapted for holding a dental mill blank of a second shape. In some such embodiments, the first shape is a puck, and the second shape is a rectangle. In some embodiments, the shaped dental blank comprises a frame. In other embodiments, the shaped dental blank is frameless.

Described herein are several alternative embodiments and methods for adapting a traditional dental milling machine for engaging dental blanks having a first shape, for use with a dental mill blank having a second (and different) shape. For example, the disclosure herein focuses on an adapter and/or modified mill blanks for use in traditional milling machines designed for "puck"-shaped dental blanks which allows those machines to be used with other types and shapes of dental blanks. These alternative embodiments include, but are not limited to, embodiments using an adapter to house a framed dental blank, using an adapter to house a frameless dental blank, and an adapter-free, frame-free, non-puck dental blank. In most embodiments, existing dental mills need not be modified in any way.

Figure 1:
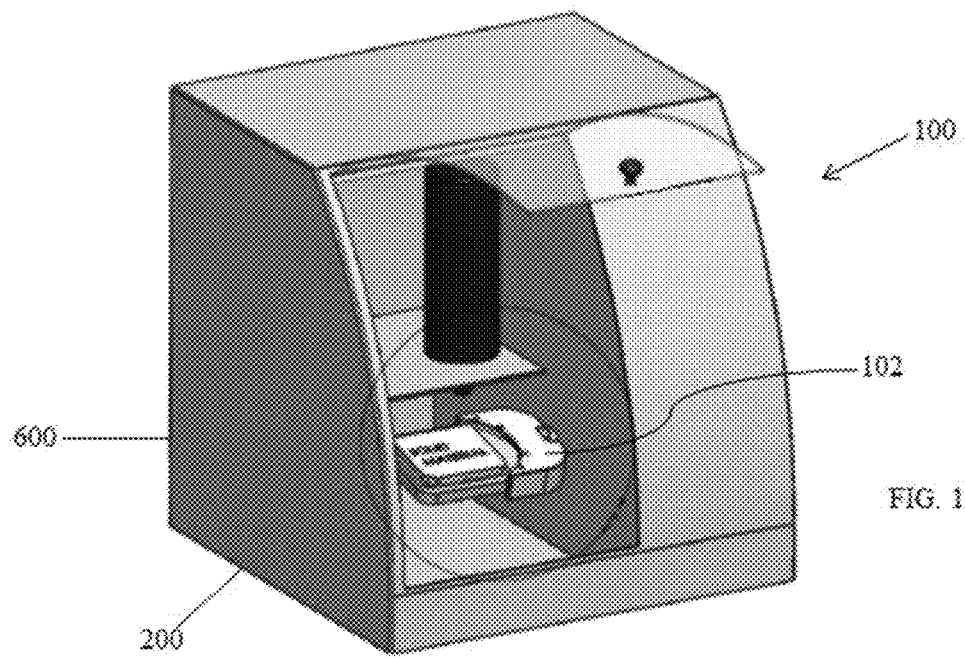
FIG. 1 is a perspective view of a dental milling machine employing an adapter in accordance with some embodiments described herein.
Figure 1A:
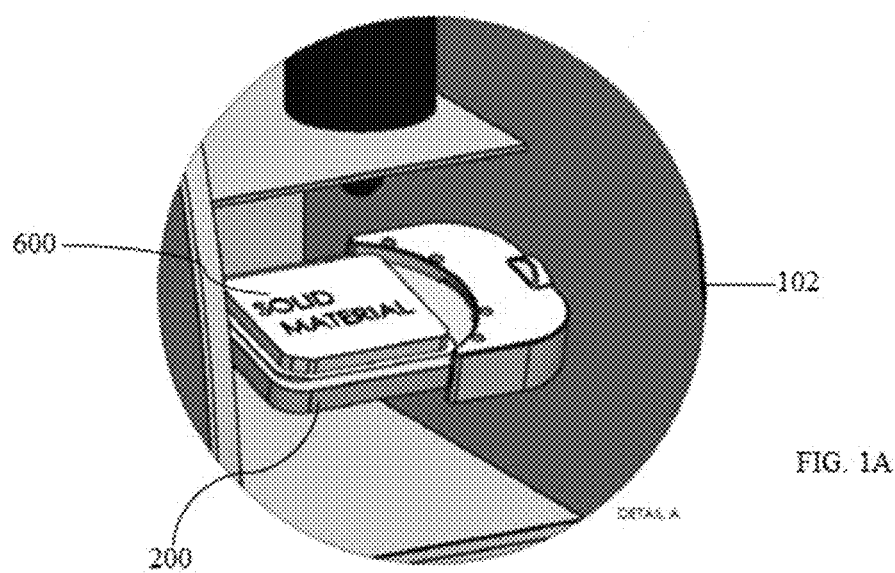
FIG. 1A is a close-up perspective view of the dental milling machine of FIG. 1.

FIG. 1 depicts a current dental milling machine 100. The milling machine 100 includes a blank receiver 102 for holding and manipulating the milling blank material during the milling operation. Shown here, and in the detail view FIG. 1A, an adapter 200 is used to hold a frameless rectangular milling blank 600. As depicted, no modification of the underlying milling machine 100 is required.

Figure 2:
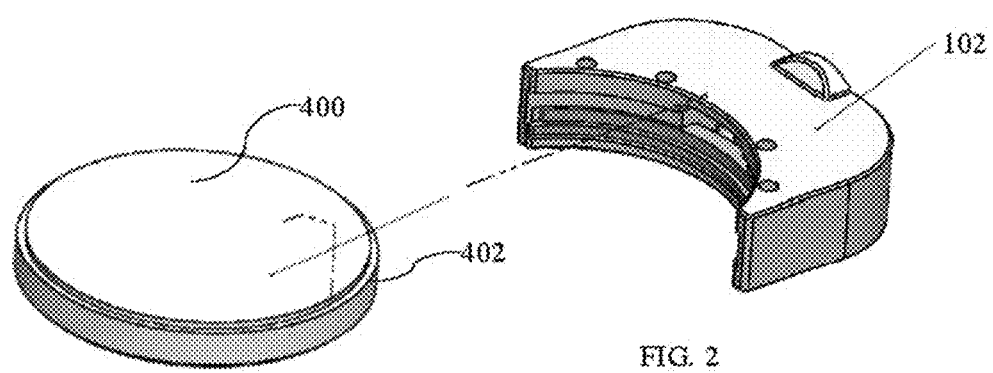
FIG. 2 is an exploded view of a receiver and a puck from a typical milling machine.

FIG. 2 shows a detailed view of the receiver 102 and a "puck" milling blank 400. The receiver 102, as shown, is just one example such as those found on Jensen milling machines. Internally a clamping system is provided for engaging and holding the blank material in place. Any suitable holding system or method may be used. The puck milling blank 400 is a solid piece of milling material and is provided with a locating flange 402 which is used to engage the receiver 102 for clamping, but is also precisely located via the locating flange 402 in accordance with the milling machine 100 parameters to ensure the block is positioned for precision milling.

Figure 3:
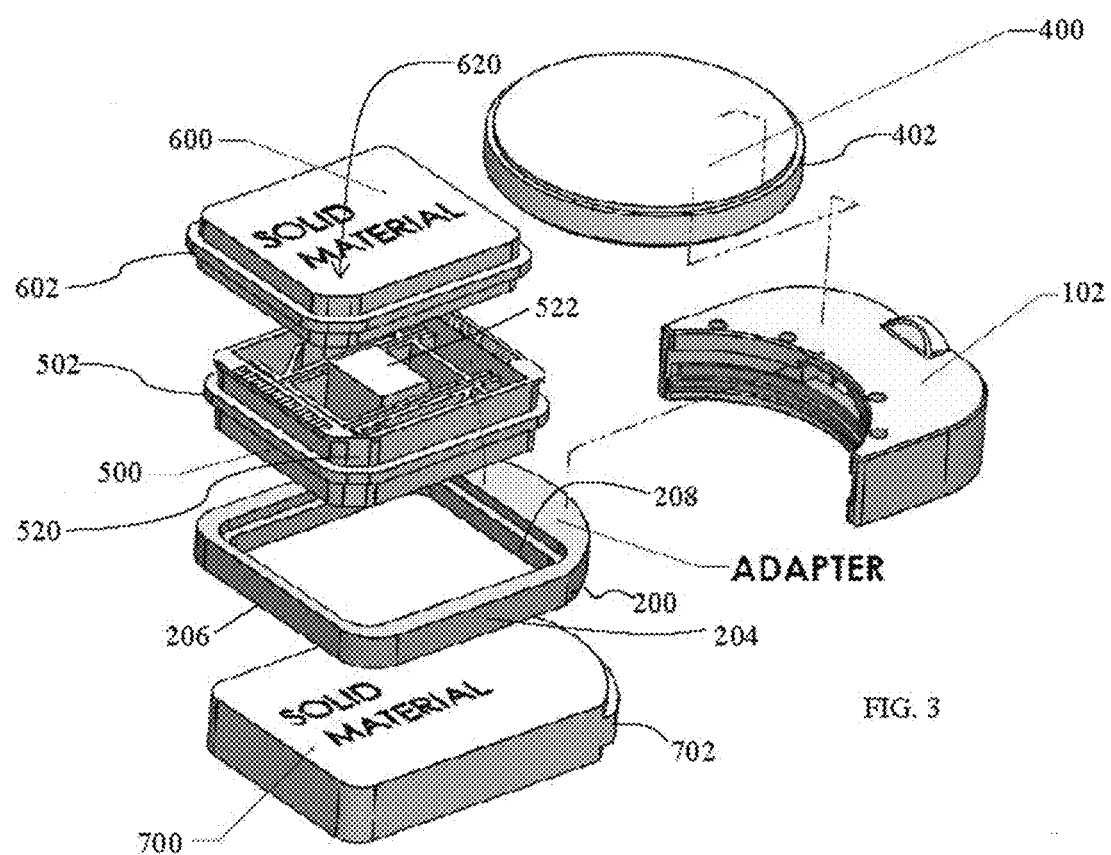
FIG. 3 is a perspective exploded view of several embodiments of the adapter and milling materials of embodiments disclosed herein.

FIG. 3 shows several alternative milling materials for use in the same, standard receiver 200. As described above, the standard puck milling blank 400 is shown. puck milling blank 400 is received and held in place in the receiver 102. Although the puck dental mill blank is popular in the dental industry, other non-puck mill blanks are also in use.

Figure 6:
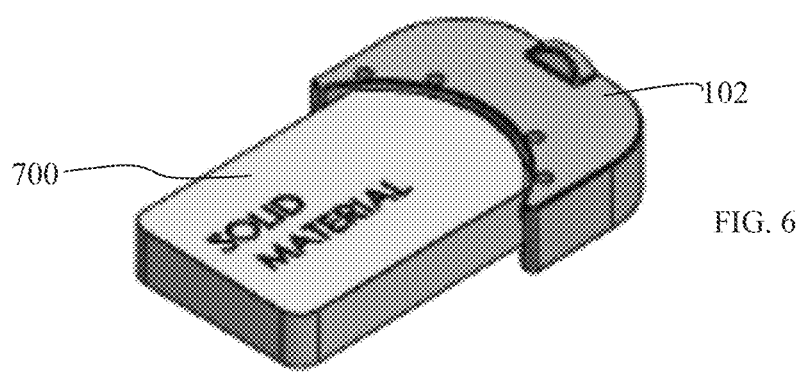
FIG. 6 is a perspective view of a non-puck, frameless solid dental mill blank in accordance with some embodiments disclosed herein.

In some embodiments, an adapter 200 is provided to hold a milling blank while engaging the receiver 102. The adapter 200 is sized and configured to hold any of a variety of milling blanks, particularly framed milling blanks 500, such as those available from 3M under the LAVA brand name. In other embodiments, the adapter can hold a frameless solid mill blank 600. In yet another embodiment, as shown in FIG. 6, a frameless, adapterless mill blank 700 can be sized and configured such that it can be engaged directly by the receiver 102. Notably either, but not both, the framed blank 500 or the solid mill blank 600 are placed in the adapter at any given time, just as either the adapter 200 or the frameless, adapterless mill blank 700, but not both, are engaged in the receiver 102 at any given time. The sizes and shapes shown correspond to current commercial sizes and shapes, but could be altered without deviating from the scope and spirit of this disclosure.

Figure 4:
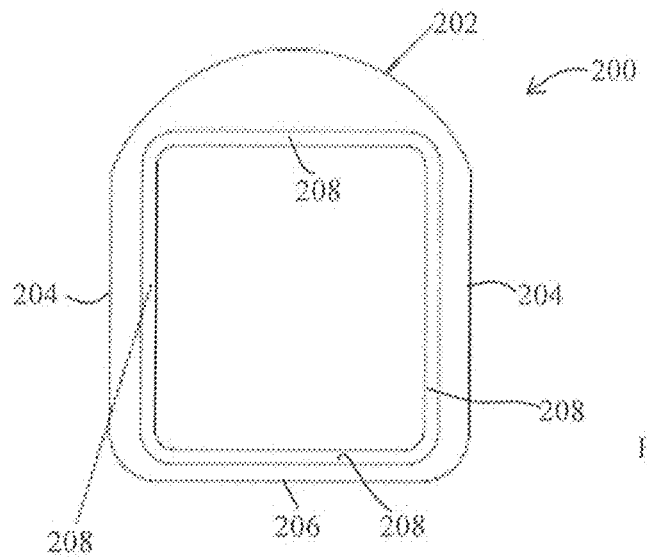
FIG. 4 is a plan view of an adapter according to some embodiments.
Figure 5:
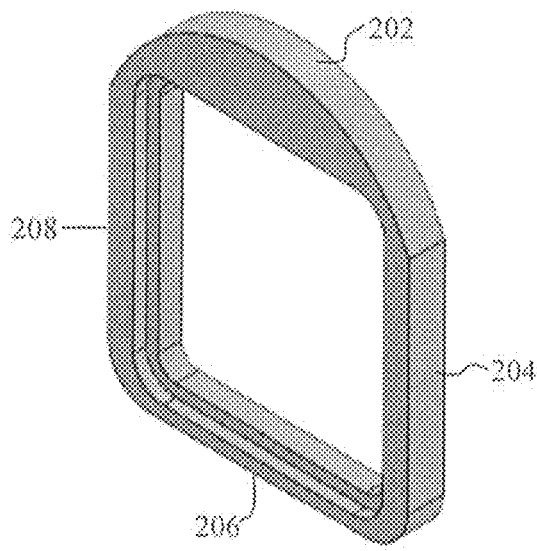
FIG. 5 is a perspective view of an adapter according to some embodiments.

The adapter 200, as shown in FIG. 3 and further detailed in FIGS. 4 and 5, comprises two side walls 204, an end wall 206 and a receiver end 210 having a locating flange 202. The two side walls 204, end wall 206, and receiver end 210 define the periphery of an aperture for receiving and holding a framed mill blank 500 or a frameless mill blank 600. A support shoulder 208 is provided on the inner surfaces of at least the two sidewalls 204, and preferably also the end wall 206 and/or the receiving end 210. The support shoulder 208 is sized and configured to support a corresponding support lip 502 on the framed mill blank 500 or support lip 602 on the frameless mill blank 600.

The framed mill blank 500 or the frameless mill blank 600 can be secured in the adapter 200 in any suitable manner. For example, but not limited to, the blank may be held in place by frictional fit, use of hardware, clamps, bolts, springs, etc.

The adapter 200 is further provided with a locating flange 202 on its receiver end. The exterior of the receiver end is rounded to accommodate the shape of the receiver 102 and is provided with a locating flange 202 for receipt into and engagement by the receiver 102. As shown, the locating flange 202 is simply a function of the size and shape of the receiver end wall 206 for receipt in the receiver, as such the receiver end wall has a curved outer surface for engaging the receiver 102. In some embodiments, locating flange 202 may be a projection distinguishable from the body of the adapter. Regardless of the arrangement, the locating flange 202 works in conjunction with the support shoulder 208 to ensure that the milling blank is in the proper location for precision milling in accordance with mill specifications.

Figure 14:
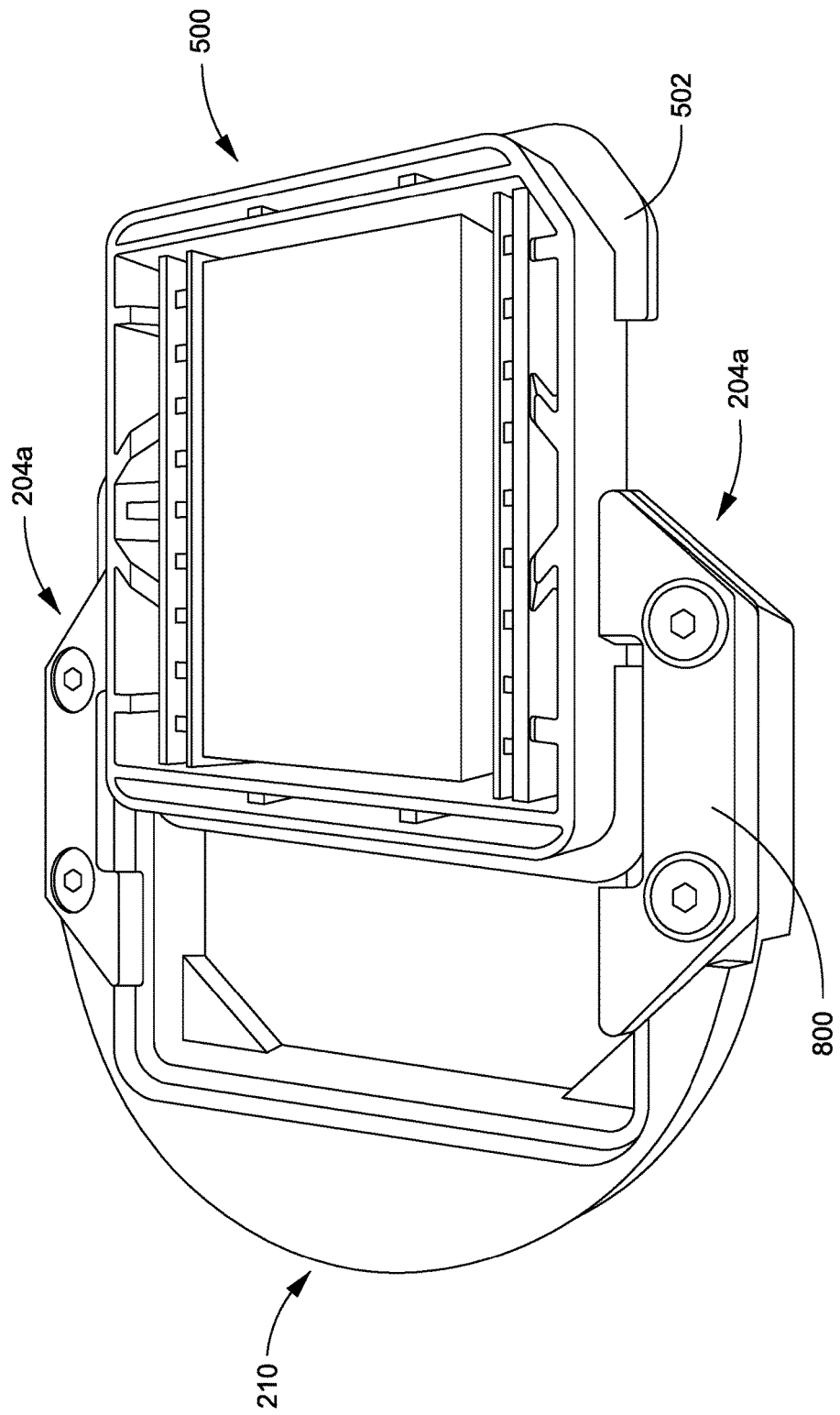
FIG. 14 is a perspective view of one embodiment with a mill blank partially in place.
Figure 15:
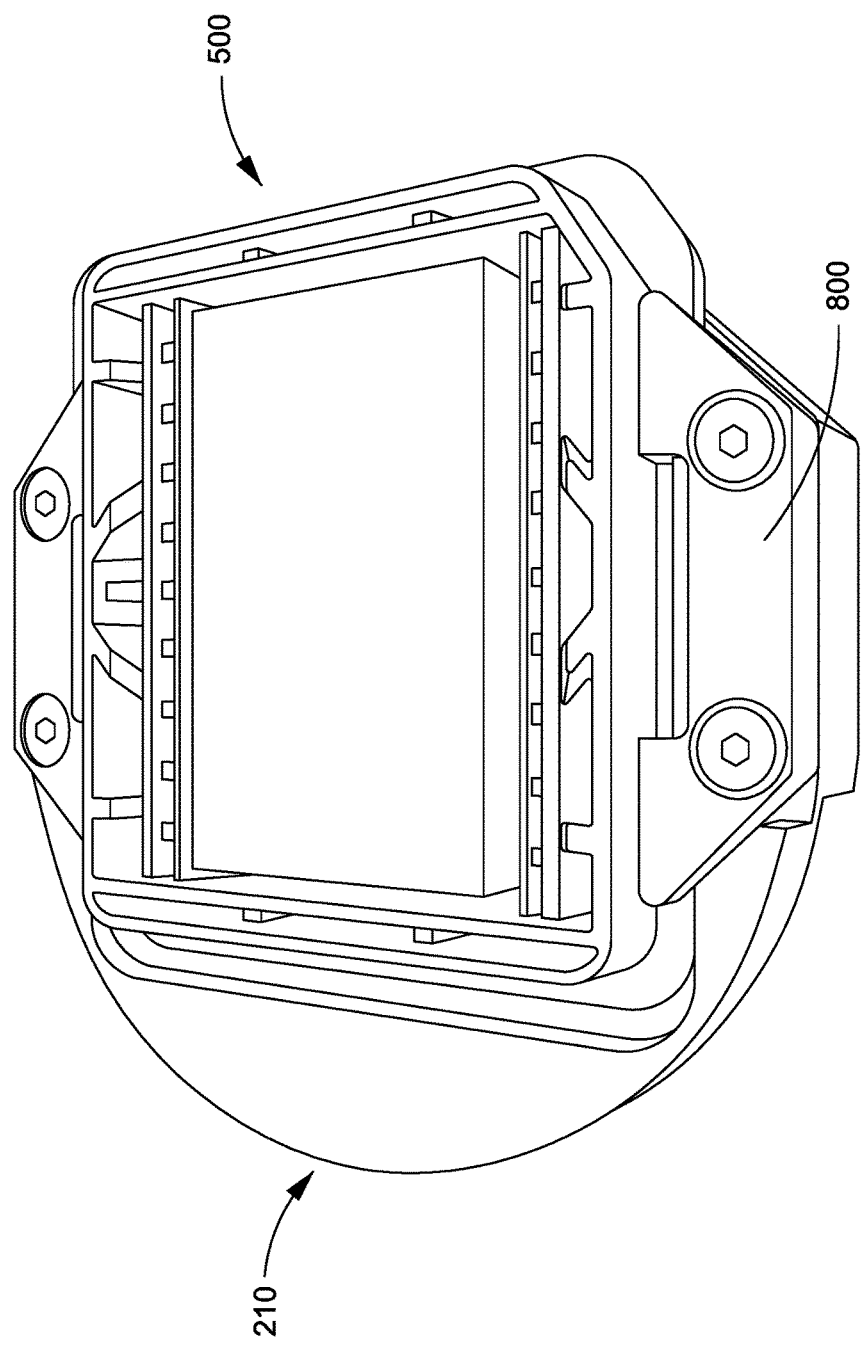
FIG. 15 is a perspective view of the embodiment of FIG. 14 with the mill blank in operation position.

In some embodiments, the adapter 200 could be open ended. That is, end wall 206 is optional. In such embodiments, the two sidewalls 204 could be biased inward so as to create a frictional engagement of the milling blank 500, 600. In some embodiments, securing systems such as those described above may be used instead of or in addition to such a frictional system. FIGS. 13-15 show a similar embodiment, although additional and optional elements are shown in those figures and described further below.

The adapter 200 may be designed and configured to hold and secure suitable mill blanks which exist on the market today. The framed milling blank 500, for example, in addition to support lip 502 is provided with sidewalls and inner ribs, which hold and support the milling material 522 from which the restoration is formed. The frame further defines an orientation geometry 520, which in its native milling machine can be used to ensure it is properly installed. This orientation geometry 520 can be replicated in the adapter or not (as shown). In frameless blanks 600, the support lip 602 is formed directly from milling material, and other features, such as the orientation geometry 620 can be formed directly in the milling material if desired.

The milling material itself can be any suitable dental milling material, including ceramic, metals, or specialty materials.

The use of the adapter and alternative mill blank designs disclosed herein allow a dental mill operator a wide variety of choices of milling blanks, while using a single mill, and without having to change receivers, if that is possible on a particular mill. With the adapters disclosed herein, a dental mill operator, previously limited to puck mill blanks, can easily switch between puck mill blanks, and framed mill blanks. The unique design of the adapter allows the user to change to a non-puck mill blank in the same manner one would change from one puck to another, no additional tools or time is necessary.

In use, the mill operator would remove any used blank material from the receiver. In preparing for a new milling operation, the operator would choose the type of milling blank to be used. In the event a puck blank is desired, the operator proceeds as usual, simply inserting a puck blank into the receiver and securing it for use. If, for example, a framed mill blank is desired, the operator selects the desired frame, and places and secures it in an adapter as described herein. The entire assembly is then inserted into the receiver, just as if it were a puck blank. The operator may then mill the material into the desired shape. When finished, the operator has at least two options for removing the blank. The entire adapter and blank can be removed, leaving only the original receiver in the mill or, the blank material may be removed from the adapter, and the adapter left in position for the next use. In this way, for those labs or offices that use non-puck blanks frequently, the adapter can be left in position and the milling material inserted, the option for milling puck blanks, however, is maintained. The use of the adapter allows for improved flexibility of the overall system.

It should be appreciated that the above description relates to particular embodiments and that an adapter can be modified and adapted for use in a variety of milling machines, taking into account the particular requirements of such machines and the mill blanks used therein. For example, the receiver 102 shown employs a clamping arrangement for holding the mill blank in place. Other attachment mechanisms could be used. In some embodiments, the adapter will take into account the particular mounting arrangement of the particular milling machine.

It will also be appreciated that the concept of providing an adapter to fit existing puck dental mills to accept non-puck dental materials is suitable for use in a variety of dental mills, having a wide variety of shapes, sizes, and configurations.

For example, the mill described above uses a blank receiver that grasps the puck from one side. At an opposite side, the blank receiver is affixed to the mill for manipulation in accordance with the desired milling operations. In other mills, the blank receiver may encircle the dental puck, may be affixed to the mill at multiple locations, or perhaps a central location above or below, or to the side of the material. Any number of permutations are possible. Above, we described an adapter that is engaged on one end by the blank receiver and forms essentially a rectangular frame for accepting the milling material or framed milling material. In alternative embodiments, the adapter is essentially U-shaped for accepting the same types of material but having an open end. It should be noted that such geometries are illustrative only. In a different mill configuration, the blank receiver of the mill could be affixed to the mill at, e.g., opposite sides. In such a case, an adapter would be made to fit within the particular blank receiver, while maintaining the proper alignment and registry of the milling material within the blank receiver. In some instances, the blank receiver itself can be modified, such that a blank receiver and separate adapter are not needed. Essentially, the blank receiver and the adapter are integral.

Figure 7:
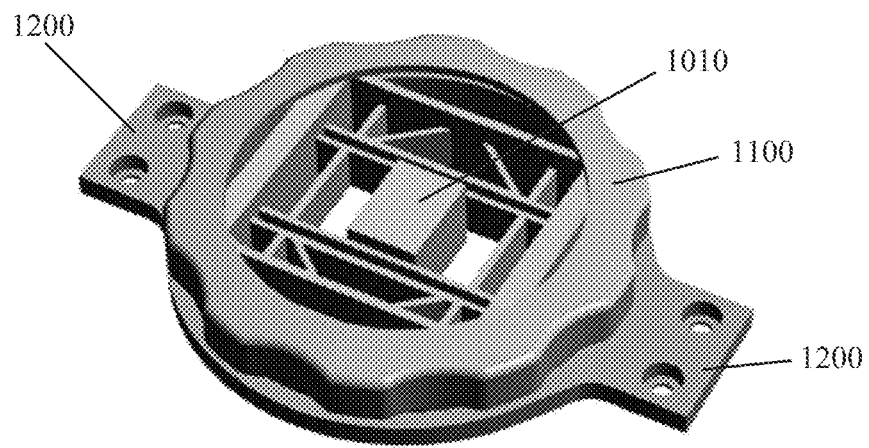
FIG. 7 is a perspective view of an adapter in accordance with another embodiment.
Figure 8:
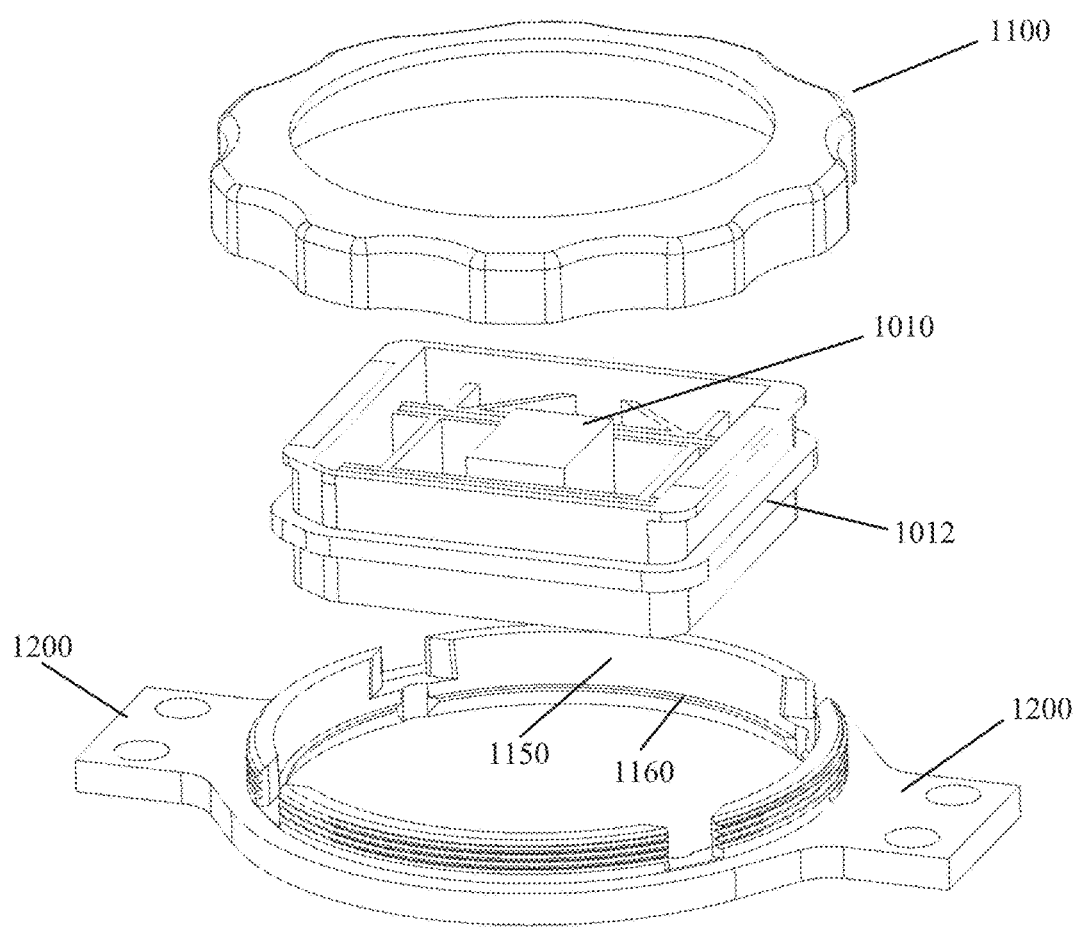
FIG. 8 is an exploded view of the adapter of FIG. 7.
Figure 9:
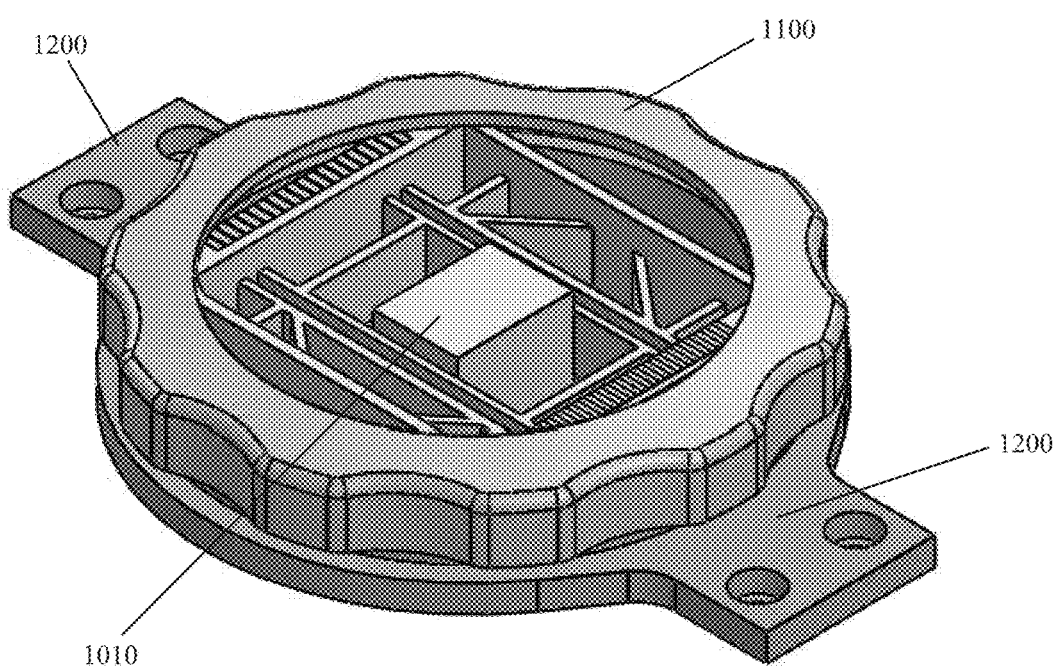
FIG. 9 is a further perspective view of an adapter in accordance with some embodiments.

FIGS. 7-9 show an adapter for a DWX-50 from Roland DGA Corporation. In this device, a blank receiver completely encircles the puck milling material, in this case a framed blank 1010, and is provided with a screw-on top portion 1100 to secure the puck into the blank receiver. At substantially opposite ends, the blank receiver is provided with flanges 1200 for affixing the blank receiver to the milling machine. The blank receiver is also provided with a cylindrical sidewall 1150, which further includes a locating flange 1160 which engages a mated flange 1012 in the puck milling material 1010 such that the milling machine knows the location of the milling material within the blank receiver. In accordance with some embodiments, an adapter is provided to replace the stock blank receiver. The adapter mimics the mounting flanges for affixing to the mill for manipulation during the milling process, and also is provided with a cylindrical sidewall mimicking the shape of the original blank receiver and allowing for proper fit and operation. Because the adapter is suited to accepting framed or frameless rectangular blank material, the question is how to insert the rectangular material into a circular hole and maintain the proper alignment. As can be seen in FIGS. 7-9, the adapter in accordance with this embodiment is provided with a plurality of slots, shown approximating the location of the corners of the framed blank material. Since the frame is made to certain known specifications, these slots can be precisely measured and positioned to place the blank material in the proper location. In the embodiment show, the blank material frame extends beyond the circumference of the cylindrical sidewall, thus necessitating the use of slots. In some instances, the adapter could be sized and configured such that the blank fits within the interior circumference of the adapter. In this case, the interior sidewall can be provided with a circumferential locating flange which mates with a complementary flange on the exterior sidewall of the blank material or frame. In some embodiments, the adapter can be provided with both the circumferential locating flange and the plurality of slots and thereby be able to accept puck material, large rectangular (framed or unframed) material, or smaller rectangular material. It is further contemplated that a small blank could also be milled in such an adapter by providing a sub-adapter (not shown) which essentially engages the small blank material and is provide with either a rectangular frame or a circular frame which is either sized to engage the slots for proper alignment or to engage the locating flange, again for proper alignment.

Those of skill in the art will readily recognize that any combination of shapes and sizes can be employed. Most common in the industry, however, are round pucks and rectangular blocks (framed and unframed). Thus, conversion from pucks to rectangles is especially useful. Any geometric or other shape can be used for either the adapter or the blank receiver.

Figure 10:
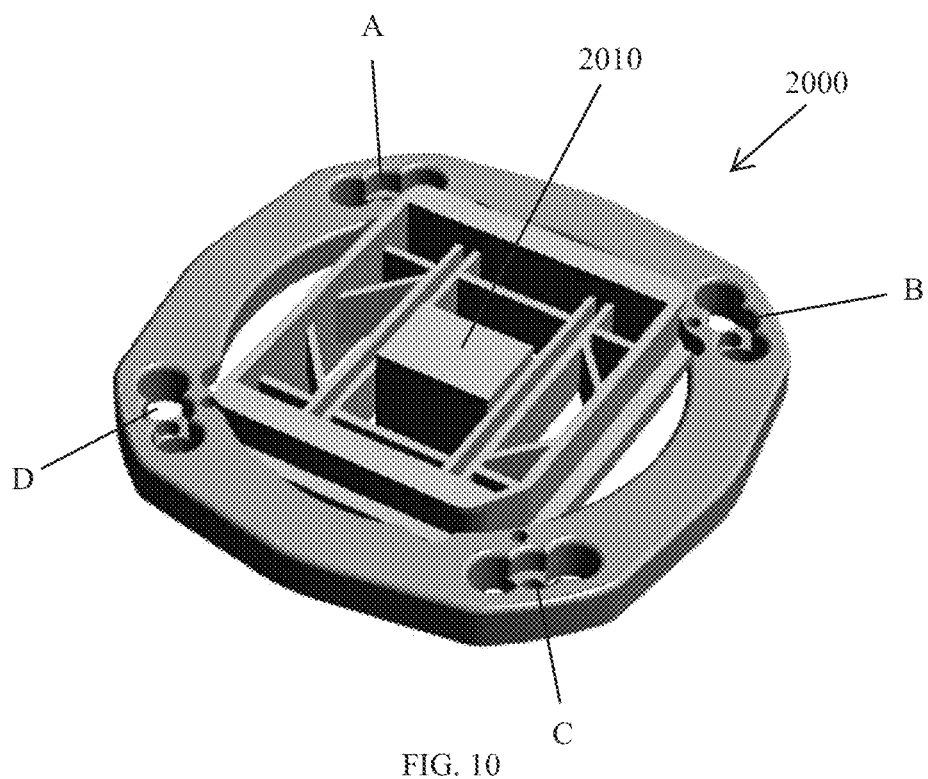
FIG. 10 is a further perspective view of an adapter in accordance with some embodiments.
Figure 11:
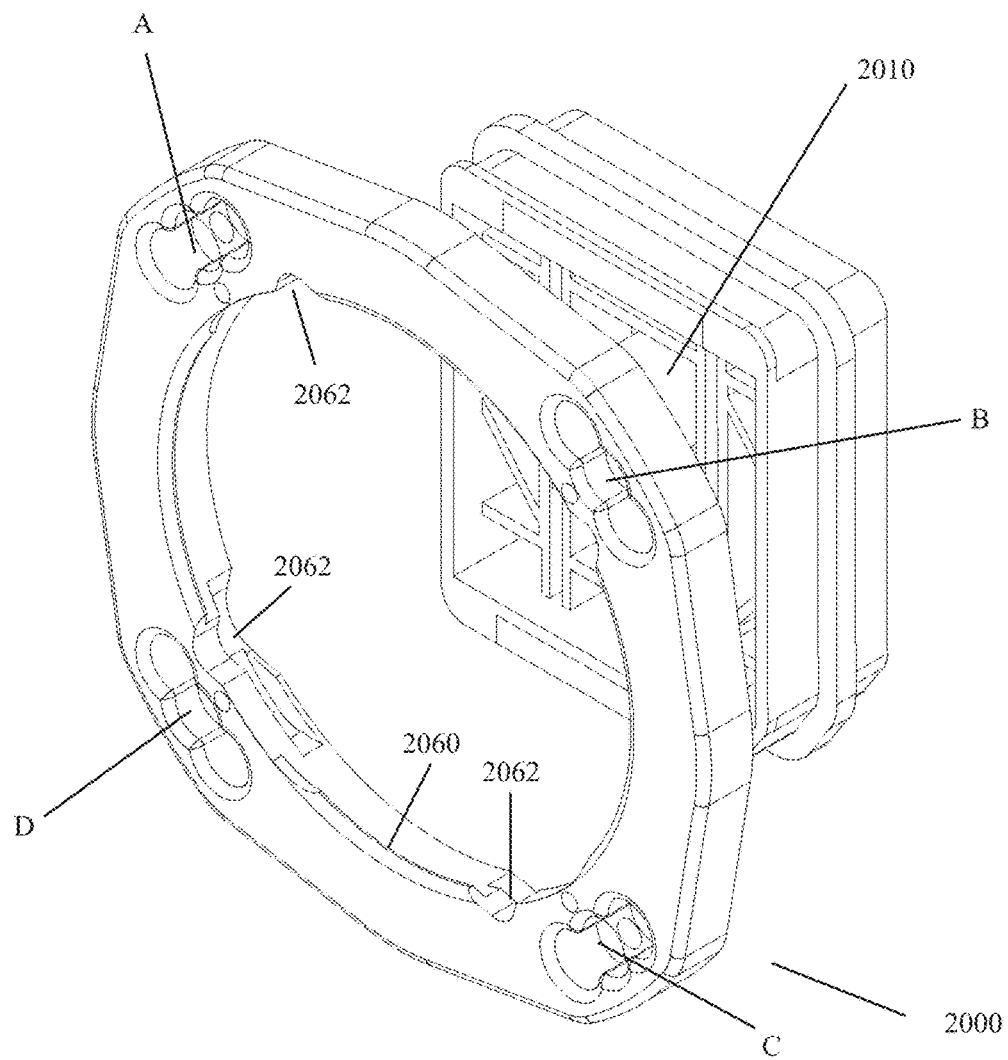
FIG. 11 is a further perspective view of an adapter in accordance with some embodiments.
Figure 12:
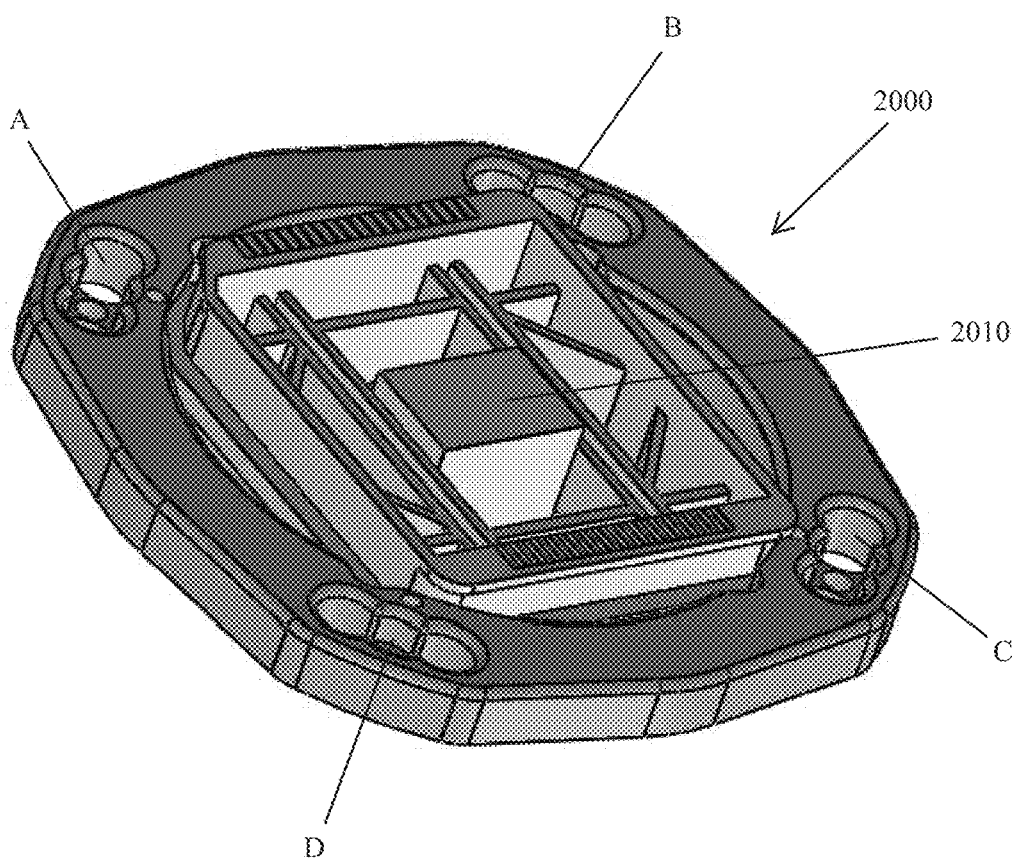
FIG. 12 is a further perspective view of an adapter in accordance with some embodiments.

As noted above, milling machines come in a variety of shapes and sizes and different configurations, but all mill industry standard materials, referred to herein as puck. Thus, FIGS. 10-12 shows another adapter for use in another generally available mill. We note again that the example is illustrative only, and the principles disclosed here can be employed to create any number of adapters for use in a particular situation.

FIGS. 10-12 show an adapter suited for use in a Zenotec Select milling machine from Wieland Dental+ Technik GmbH & Co. KG. Notably, the adapter 2000 is again a unified blank receiver and adapter. In this instance, the adapter is suitable for attachment to the mill at four locations (A, B, C, D). The adapter defines a generally circular aperture for accepting puck material. As with prior designs, a locating flange 2060 may be used for proper placement and alignment of the material. In this embodiment, the locating flange 2060 is defined by a lower portion of the adapter. Notches 2062 are provided in the generally circular sidewall to allow for the corners of framed block material 2010 to pass therethrough. Because the adapter has a height or thickness associated with it, it may be necessary to provide further notches or slots in the adapter sidewalls to accommodate the corners of the rectangular blank material or frame. As with prior designs, a locating flange on the blank material engages a locating flange on the adapter to facilitate proper alignment. As discussed above, many permutations on this theme are possible.

Due to the wide variety of mills available and already in place in the market suitable for a single type of blank material and the advancement of framed blank materials, there is a real need for adapters to allow existing mills to operate with the standard puck materials, and the ever increasingly popular framed material. The adapters disclosed herein fulfill a real and unmet need in the marketplace.

FIGS. 13-15 show yet another embodiment. Similar to the embodiment shown in FIGS. 4 and 5, this variation has a horseshoe configuration and also shows an alternative clamping arrangement. The clamping arrangement can be used in any other embodiment, just as other clamping or holding means may be used in the horseshoe configuration.

Figures 13A, 13B:
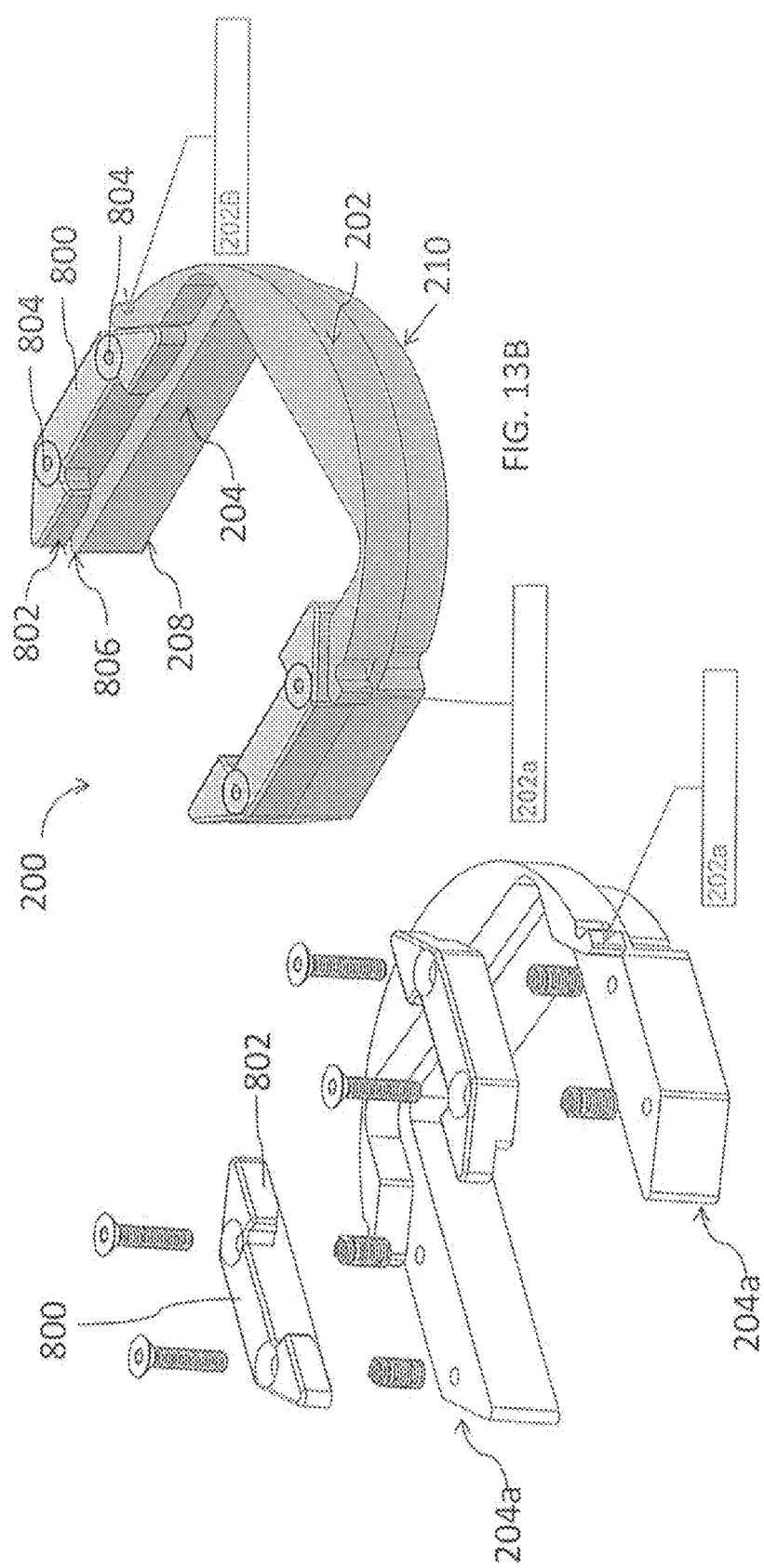
FIG. 13A is an exploded, perspective view of one embodiment described herein.
FIG. 13B is a perspective view of the embodiment shown in FIG. 13A.

As shown in FIGS. 13A and 13B, this embodiment comprises two sidewalls 204, a receiver end wall 210, optionally having a locating flange 202, but does not include an end wall corresponding to end wall 206 in FIGS. 4 and 5. The two side walls 204 and the receiver end wall 210 define the periphery of an aperture for receiving and holding a framed mill blank 500, as shown in FIGS. 14 and 15, or could accept a frameless mill blank as described above. In this embodiment, sidewalls 204 are part of the side arms 204a. Similar to the embodiments described above, a support shoulder 208 is provided on the inner surfaces of at least the two sidewalls 204, and optionally on the receiving end 210. As with other embodiments, the support shoulder 208 is sized and configured to support the corresponding support lip 502 on the framed mill blank 500 or the support lip on a frameless mill blank. As with other embodiments, the receiving end 210 can be mounted into the mill by any suitable means, and particularly is meant to be mounted in a manner similar to the original blank material shape (e.g., a puck) despite the difference in shape of the blank material held in the adapter.

FIGS. 13A and 13B also detail an alternative clamping arrangement used to secured the blank material in the adapter. Although illustrated in this horseshoe embodiment, the clamping arrangement can be used in any embodiment. As shown, a selectively removable and adjustable clamping member 800 is oriented substantially longitudinally along one or both side arms 204a defining sidewalls 204 and defining a portion thereof. The clamping member 800 is provided with a lateral projection 802 substantially parallel with the support shoulder 208 and defining a space 806 therebetween. The space 806 is sized and configured to accept the support lip 502 of the blank material. As shown, screws or bolts 804 are used to secure the clamping member to the sidewall thereby securing the blank material 500 against movement during milling operations. FIG. 13A and FIG. 13B also show optional wings 202a and 202b, which minimize or prevent rotation of the adaptor in the mill. The wings 202a and 202b may be any suitable shape or configuration to prevent unwanted rotation. Optional crossbraces or angular supports (not shown) may also be provided connecting the arms 204a and 204b to the receiving end 210 to provide added rigidity to the frame. FIG. 14 shows a framed mill blank 500 with support lip 502 being slid into place along support shoulder 208 in the space 806 between the clamping member's lateral projection 802 and the support shoulder 208. Alternatively, one or both of the clamping members 800 could have been removed, and the blank material dropped in place. This arrangement allows for that flexibility depending on the space in a particular mill. FIG. 15 shows the framed mill blank 500 in an operational position. Those of skill in the art will readily recognize that many different shapes and arrangement may be employed. As shown, each side arm is provided with a fully removable and adjustable clamping member. It is contemplated that in some embodiments, one of the clamping member could be static, with the milling blank inserted into the space defined by the static clamping member and the support surface on one side and then secured by an adjustable clamping member on the other. It is also contemplated that one or more of the clamping members need not be fully removable, but rather adjustable to be tightened to secure the mill blank. It is further contemplated that a plurality of clamping members may be employed. Further, any suitable means may be used to provide the necessary clamping power. As shown, screws or bolts are employed. In some embodiments, other methods such as hinges, springs, latches, etc. could be employed.

Although the present invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

We claim:

1. A mill blank assembly for use in a dental milling machine having a dental blank receiver for engaging dental blanks having a first shape, said mill blank assembly comprising:
   mill blank material comprising a singular unit having a second shape; and
   an adapter for holding the mill blank material, the adapter comprising:
   a receiver end wall adapted to engage the receiver of the dental milling machine; and
   two side walls adapted for holding the mill blank material; wherein the two side walls are opposite each other and extending from the receiver end wall; wherein the two side walls and the receiver end wall define peripheral walls of an aperture for receiving the mill blank material; wherein the peripheral walls are provided with a support shoulder for engaging a support lip of the mill blank material.

2. The mill blank assembly of claim 1, wherein the mill blank material comprises a framed mill blank.

3. The mill blank assembly of claim 1, wherein the mill blank material comprises a frameless mill blank.

* * * * *